US010206977B1

(12) United States Patent
Koob et al.

(10) Patent No.: US 10,206,977 B1
(45) Date of Patent: *Feb. 19, 2019

(54) ISOLATED PLACENTAL STEM CELL RECRUITING FACTORS

(71) Applicant: MiMedx Group, Inc., Marietta, GA (US)

(72) Inventors: Thomas J. Koob, Marietta, GA (US); Rebeccah J. C. Brown, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/157,445

(22) Filed: Jan. 16, 2014

Related U.S. Application Data

(60) Provisional application No. 61/962,313, filed on Jan. 18, 2013.

(51) Int. Cl.
- *A61K 38/17* (2006.01)
- *A61K 35/50* (2015.01)
- *A61F 2/02* (2006.01)

(52) U.S. Cl.
CPC .............. *A61K 38/17* (2013.01); *A61F 2/02* (2013.01); *A61K 35/50* (2013.01)

(58) Field of Classification Search
None
See application file for complete search history.

(56) References Cited

U.S. PATENT DOCUMENTS

| | | | |
|---|---|---|---|
| 2,694,914 A | 11/1954 | Glover, Jr. | |
| 3,272,204 A | 9/1966 | Artandi | |
| 3,885,320 A | 5/1975 | Hodson et al. | |
| 4,564,368 A | 1/1986 | Sawyer et al. | |
| 4,703,108 A | 10/1987 | Silver et al. | |
| 4,745,771 A | 5/1988 | Linner et al. | |
| 4,807,442 A | 2/1989 | Linner et al. | |
| 4,847,049 A | 7/1989 | Yamamoto | |
| 4,865,871 A | 9/1989 | Livesey et al. | |
| 4,964,280 A | 10/1990 | Piunno et al. | |
| 4,968,325 A | 11/1990 | Black et al. | |
| 5,118,867 A | 6/1992 | Bahrmann et al. | |
| 5,284,655 A | 2/1994 | Bogdansky et al. | |
| 5,541,232 A | 7/1996 | Howell et al. | |
| 5,780,295 A | 7/1998 | Livesey et al. | |
| 5,807,581 A | 9/1998 | Rosenblatt et al. | |
| 6,030,635 A | 2/2000 | Gertzman et al. | |
| 6,163,979 A | 12/2000 | Oetjen et al. | |
| 6,387,369 B1 | 5/2002 | Pittenger et al. | |
| 6,565,960 B2 | 5/2003 | Koob et al. | |
| 6,652,583 B2 | 11/2003 | Hopkins et al. | |
| 6,716,895 B1 | 4/2004 | Terry | |
| 6,936,271 B1 | 8/2005 | Oliver et al. | |
| 7,101,857 B2 | 9/2006 | Sung et al. | |
| 7,311,904 B2 | 12/2007 | Hariri | |
| 7,311,905 B2 | 12/2007 | Hariri | |
| 7,901,455 B2 | 3/2011 | Koob et al. | |
| 8,067,044 B2 | 11/2011 | Henry et al. | |
| 8,153,162 B2 | 4/2012 | Tseng et al. | |
| 8,177,839 B2 | 5/2012 | Koob et al. | |
| 8,192,481 B2 | 6/2012 | King | |
| 8,196,416 B2 | 6/2012 | Uri et al. | |
| 8,323,701 B2 | 12/2012 | Daniel et al. | |
| 8,357,403 B2 | 1/2013 | Daniel et al. | |
| 8,372,437 B2 | 2/2013 | Daniel | |
| 8,372,439 B2 | 2/2013 | Daniel et al. | |
| 8,409,626 B2 | 4/2013 | Daniel et al. | |
| 8,623,421 B2 | 1/2014 | Daniel | |
| 8,946,163 B2 | 2/2015 | Koob | |
| 8,961,617 B2 | 2/2015 | Young | |
| 2002/0123141 A1 | 9/2002 | Hariri | |
| 2002/0160510 A1 | 10/2002 | Hariri | |
| 2003/0032179 A1 | 2/2003 | Hariri | |
| 2003/0187515 A1 | 10/2003 | Hariri et al. | |
| 2004/0028711 A1 | 2/2004 | Uchida et al. | |
| 2004/0048796 A1 | 3/2004 | Hariri et al. | |
| 2006/0140913 A1 | 6/2006 | Bhatia | |
| 2006/0154860 A1* | 7/2006 | Ceradini | C07K 14/4702 514/44 R |
| 2006/0166361 A1 | 7/2006 | Seyda et al. | |
| 2006/0210532 A1 | 9/2006 | Carmeliet et al. | |
| 2006/0233850 A1* | 10/2006 | Michal | A61L 27/20 424/422 |
| 2007/0020225 A1 | 1/2007 | Abramson et al. | |
| 2007/0021704 A1* | 1/2007 | Hariri | A61F 13/069 602/48 |
| 2007/0021762 A1 | 1/2007 | Liu et al. | |
| 2007/0071740 A1 | 3/2007 | Tseng et al. | |
| 2007/0071828 A1 | 3/2007 | Tseng et al. | |
| 2007/0144062 A1 | 6/2007 | Wright | |
| 2007/0202189 A1 | 8/2007 | Ahlfors | |
| 2007/0248575 A1 | 10/2007 | Connor et al. | |
| 2007/0299043 A1 | 12/2007 | Hunter et al. | |
| 2008/0046095 A1 | 2/2008 | Daniel | |
| 2008/0050347 A1 | 2/2008 | Ichim | |
| 2008/0069895 A1 | 3/2008 | Liu et al. | |
| 2008/0131966 A1 | 6/2008 | Hariri | |
| 2008/0181967 A1 | 7/2008 | Liu et al. | |
| 2008/0233552 A1 | 9/2008 | Ma et al. | |
| 2009/0012629 A1 | 1/2009 | Yao et al. | |
| 2009/0036996 A1 | 2/2009 | Roeber | |
| 2009/0053290 A1 | 2/2009 | Sand et al. | |
| 2009/0056162 A1 | 3/2009 | McMahon et al. | |
| 2009/0092664 A1 | 4/2009 | Mumper et al. | |
| 2009/0142831 A1 | 6/2009 | Hariri | |
| 2009/0287308 A1 | 11/2009 | Davis et al. | |
| 2009/0291891 A1 | 11/2009 | Neufeld | |
| 2010/0028849 A1 | 2/2010 | Shelby et al. | |
| 2010/0104539 A1 | 4/2010 | Daniel et al. | |

(Continued)

FOREIGN PATENT DOCUMENTS

| | | |
|---|---|---|
| CN | 101433556 | 5/2009 |
| EP | 0 431 164 A1 | 6/1991 |

(Continued)

OTHER PUBLICATIONS

Inokuma et al., Stem Cells, 24:2810-2816 (2006).*

(Continued)

*Primary Examiner* — Thomas J. Visone
(74) *Attorney, Agent, or Firm* — Alston & Bird LLP

(57) ABSTRACT

Described herein are compositions and methods of using placental stem cell recruiting factors, more specifically, isolated placental stem cell recruiting factors. In one embodiment, isolated placental stem cell recruiting factors are delivered to a site such as a diseased or injured organ and/or body part in an amount sufficient to recruit stem cells to the site.

10 Claims, 4 Drawing Sheets

(56) References Cited

U.S. PATENT DOCUMENTS

| | | | |
|---|---|---|---|
| 2010/0136114 A1 | 6/2010 | Mao | |
| 2010/0143312 A1 | 6/2010 | Hariri et al. | |
| 2010/0178297 A1 | 7/2010 | Carmeliet et al. | |
| 2010/0199514 A1 | 8/2010 | Camisa | |
| 2010/0209408 A1 | 8/2010 | Stephen et al. | |
| 2010/0260847 A1 | 10/2010 | Hariri | |
| 2010/0272679 A1* | 10/2010 | Penn | A61K 38/195 424/85.2 |
| 2010/0272782 A1 | 10/2010 | Owens et al. | |
| 2010/0317677 A1 | 12/2010 | Hassel et al. | |
| 2011/0044997 A1 | 2/2011 | Rankin et al. | |
| 2011/0177150 A1 | 7/2011 | Pathak et al. | |
| 2011/0189301 A1 | 8/2011 | Yang et al. | |
| 2011/0206776 A1 | 8/2011 | Tom et al. | |
| 2011/0282448 A1 | 11/2011 | Paulos et al. | |
| 2011/0307059 A1 | 12/2011 | Young et al. | |
| 2012/0010708 A1 | 1/2012 | Young et al. | |
| 2012/0030963 A1 | 2/2012 | Durance et al. | |
| 2012/0078378 A1* | 3/2012 | Daniel | A61L 27/3604 623/23.72 |
| 2012/0135045 A1 | 5/2012 | Nixon et al. | |
| 2012/0189571 A1 | 7/2012 | Sengupta et al. | |
| 2012/0189583 A1 | 7/2012 | Liu et al. | |
| 2012/0189586 A1 | 7/2012 | Harrell | |
| 2012/0282348 A1 | 11/2012 | Yates et al. | |
| 2012/0294910 A1 | 11/2012 | Daniel et al. | |
| 2013/0095060 A1 | 4/2013 | Hsieh et al. | |
| 2013/0230561 A1 | 9/2013 | Daniel et al. | |
| 2013/0273008 A1 | 10/2013 | Lemper et al. | |
| 2014/0017280 A1 | 1/2014 | Daniel et al. | |
| 2014/0106447 A1 | 4/2014 | Brown et al. | |
| 2014/0140964 A1 | 5/2014 | Brown et al. | |
| 2014/0142025 A1 | 5/2014 | Koob | |
| 2014/0205646 A1 | 7/2014 | Morse et al. | |
| 2014/0308233 A1 | 10/2014 | Koob | |
| 2014/0356451 A1 | 12/2014 | Koob | |

FOREIGN PATENT DOCUMENTS

| | | |
|---|---|---|
| EP | 0431479 A1 | 6/1991 |
| EP | 0431164 A1 | 12/1991 |
| EP | 0 506 207 B1 | 9/1992 |
| KR | 10/1991/0011272 | 8/1991 |
| KR | 10/1991/0011727 | 8/1991 |
| KR | 2001/100588 | 11/2001 |
| WO | WO-87/00062 A1 | 1/1987 |
| WO | WO-88/03805 A1 | 6/1988 |
| WO | WO-01/00151 A1 | 1/2001 |
| WO | WO-01/08716 A1 | 2/2001 |
| WO | WO-2004/026244 A2 | 4/2004 |
| WO | WO-2005/017165 | 2/2005 |
| WO | WO-2007/010305 | 1/2007 |
| WO | WO-2007/076522 | 7/2007 |
| WO | WO-2007/083984 A1 | 7/2007 |
| WO | WO-2009/033160 A1 | 3/2009 |
| WO | WO-2009/048908 | 4/2009 |
| WO | WO-2009/132186 A1 | 10/2009 |
| WO | WO-2010/029344 A2 | 3/2010 |
| WO | WO-2011/103470 | 8/2011 |
| WO | WO-2011/127117 | 10/2011 |
| WO | WO-2012/003377 | 1/2012 |
| WO | WO-2012/065937 A1 | 5/2012 |
| WO | WO-2012/069559 A1 | 5/2012 |
| WO | WO-2012/112410 A2 | 8/2012 |
| WO | WO-2012/112417 A2 | 8/2012 |
| WO | WO-2012/112441 A1 | 8/2012 |
| WO | WO-2013/095830 A1 | 6/2013 |

OTHER PUBLICATIONS

MyBioSource <http://www.mybiosource.com/prods/Recombinant-Protein/CCL27-CTACK/datasheet.php?products_id=444008>Accessed Jun. 9, 20015).*
Zaja-Milatovic et al., Histol. Histopathol., 23(11):1399-1407 (2008).*
Nibbs et al (Expert Opin. Biol. Ther., 3(1):15-22 (2003).*
EPIFIX brochure (2009).*
Coulomb-L'Hermine et al (AIDS Res. Hum. Retro., 16(11):1097-1098 (2000).*
Rabbany et al., Cell Transplant., 19:399-408 (2010).*
Ahmed et al.,Placenta, 21(14A):S16-S24 (2000).*
U.S. Appl. No. 13/647,308, filed Oct. 8, 2012, Daniel et al.
U.S. Appl. No. 13/688,091, filed Nov. 28, 2012, Spencer et al.
U.S. Appl. No. 13/719,148, filed Feb. 13, 2012, Morse et al.
U.S. Appl. No. 13/744,331, filed Jan. 17, 2013, Koob et al.
U.S. Appl. No. 13/744,332, filed Jan. 17, 2013, Pringle et al.
U.S. Appl. No. 13/745,642, filed Jan. 18, 2013, Koob et al.
U.S. Appl. No. 13/787,612, filed Mar. 6, 2013, Morse et al.
U.S. Appl. No. 13/815,747, filed Mar. 15, 2013, Daniel et al.
U.S. Appl. No. 13/815,753, filed Mar. 15, 2013, Koob et al.
U.S. Appl. No. 13/815,784, filed Mar. 15, 2013, Koob et al.
U.S. Appl. No. 13/815,873, filed Mar. 15, 2013, Brown et al.
U.S. Appl. No. 13/963,984, filed Aug. 9, 2013, Daniel et al.
U.S. Appl. No. 13/967,326, filed Aug. 14, 2013, Koob et al.
U.S. Appl. No. 13/983,301, filed Aug. 1, 2013, Morse et al.
U.S. Appl. No. 14/050,218, filed Oct. 9, 2013, Brown et al.
"MiMedx Group Announces Launch of EpiFixTM and Hiring of Vice President, Wound Care," Mimedx Press Release (2011).
Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
EpiFix Product Brochure (2011).
Hannallah et al., "Cerebrospinal fluid leaks following cervical spine surgery," J. Bone Joint Surg. Am., (2008), 90(5):1101-1105.
Hattori et al., "Placental growth factor reconstitutes hematopoiesis by recruiting VEGFR1+ stem cells from bone-marrow microenvironment," Nat. Med., (2002), 8(8):841-849.
Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.
Koob et al., "Biological properties of dehydrated human amnion-chorion composite graft: implications for chronic wound healing", International Wound Healing, 2013, 10(5):493-500.
Mayfield et al., "Watertight closure of spinal dura mater: Technical note," J. Neurosurg., (1975), 43(5):639-640.
PCT International Preliminary Report on Patentability for copending PCT Application No. PCT/US2012/024798, dated Feb. 1, 2013.
PCT International Search Report and Written Opinion for copending PCT Application No. PCT/US2013/064146, dated Jan. 9, 2014.
PCT International Search Report and Written Opinion for copending PCT Application No. PCT/US2013/054319, dated Nov. 13, 2013.
PCT International Search Report and Written Opinion for copending PCT Application No. PCT/US2013/055003, dated Nov. 19, 2013.
PCT International Search Report and Written Opinion for copending PCT Application No. PCT/US2013/054320, dated Nov. 6, 2013.
PCT International Search Report and Written Opinion for copending PCT Application No. PCT/US2013/054322, dated Oct. 22, 2013.
PCT International Search Report and Written Opinion for copending PCT Application No. PCT/US2012/66862, dated Feb. 12, 2013.
PCT International Search Report and Written Opinion for copending PCT Application No. PCT/US2013/054325, dated Oct. 28, 2013.
PCT International Search Report for copending PCT Application No. PCT/US2012/024798, dated Jun. 20, 2012.
Tao, et al., "Implantation of amniotic membrane to reduce postlaminectomy epidurla adhesions," Eur. Spine. J., (2009), 18:1202-1212.
Bauer S.M., et al., "Angiogenesis, vasculogenesis, and induction of healing in chronic wounds." Vascular and endovascular surgery 2005, 39:293-306.
Bennett JP, et al., "Treatment of chronic ulceration of the legs with human amnion." Lancet 1980, 1:1153-1156.

(56) References Cited

OTHER PUBLICATIONS

Blakytny R.,"The molecular biology of chronic wounds and delayed healing in diabetes. Diabetic medicine" A journal of the British Diabetic Association 2006, 23:594-608.
Borkow et al., "Reducing the risk of skin pathologies in diabetics by using copper impregnated socks", Medical Hypotheses, 2009, 1-4, doi:10.1016/j.mehy.2009.02.050.
Carmeliet P, et al., "Synergism between vascular endothelial growth factor and placental growth factor contributes to angiogenesis and plasma extravasation in pathological conditions." Nature medicine 2001, 7:575-583.
Database WPI XP002732611 & KR 2001-0100588, dated Nov. 14, 2001—Abstract.
Derwent Abstract for KR 200110588, original document published Nov. 2001.
Dua H.S., et al., "The amniotic membrane in ophthalmology." Survey of ophthalmology 2004, 49:51-77.
Ennis W., et al. "Clinical experience with a novel regenerative template for hard to heal wounds." In SAWC Annual Spring Meeting; Atlanta, GA. 2012.
Extended European Search Report dated Dec. 2, 2014, for European Patent Application No. EP 12746721.
Faulk W.P., et al. "Human amnion as an adjunct in wound healing." Lancet 1980, 1:1156-1158.
Forbes J, et al., "Dehydrated amniotic membrane allografts for the treatment of chronic wounds: a case series." Journal of Wound Care 2012, 21:290, 292, 294-296.
Gruss J.S., et al. "Human amniotic membrane: a versatile wound dressing." Canadian Medical Association journal 1978, 118:1237-1246.
Hao, Y., et al., "Identification of antiangiogenic and antiinflammatory proteins in human amniotic membrane." Cornea 2000, 19:348-352.
http://proxybiomedical.com/Images/ML005-01-Rev002.pdf (accessed on Jun. 5, 2014.).
John,T., "Human amniotic membrane transplantation: past, present, and future." Ophthalmology clinics of North America 2003, 16:43-65, vi.
Kim J.C., et al., "The effects on inhibition of corneal neovascularization after human amniotic membrane transplantation in severely damaged rabbit corneas. Korean journal of ophthalmology" KJO 1995, 9:32-46.
Kim K.A., et al., "Dysfunction of endothelial progenitor cells under diabetic conditions and its underlying mechanisms." Archives of pharmacal research 2012, 35:223-234.
Koizumi N.J., et al., "Growth factor mRNA and protein in preserved human amniotic membrane." Current eye research 2000, 20:173-177.
Koob T.J., et al., "Biological properties of dehydrated human amnion/chorion composite graft: implications for chronic wound healing." International wound journal 2013, 10:493-500.
Kubo M., et al., "Immunogenicity of human amniotic membrane in experimental xenotransplantation." Investigative ophthalmology & visual science 2001, 42:1539-1546.
Li J., et al., "Angiogenesis in wound repair: angiogenic growth factors and the extracellular matrix." Microscopy research and technique 2003, 60:107-114.
Lopez-Valladares MJ, et al., "Donor age and gestational age influence on growth factor levels in human amniotic membrane." Acta ophthalmologica 2010, 88:e211-216.
Lu. et al., "Molecular mechanisms and clinical applications of nordihydroguaiaretic acid (NDGA) and its derivatives: An update," Med. Sci. Monit., (2010), 16(5):RA93-RA100.
Mermet I., et al., Use of amniotic membrane transplantation in the treatment of venous leg ulcers. Wound repair and regeneration : official publication of the Wound Healing Society [and] the European Tissue Repair Society 2007, 15:459-464.

MiMedx Press Release, "MiMedx Scientific Study is Electronically Published in the International Wound Journal", 2013.
Moussy et al., "Transport characteristics of a novel local drug delivery system using nordihydroguaiaretic acid (NDGA)-polymerized collagen fibers," Biotechnology Progress, (2007), 23(4):990-994.
Nagaya et al., "Transplantation of mesenchymal stem cells improves cardiac function in a rat model of dilated cardiomyopathy", Circulation, 2005, 112(8):1128-1135.
Parolini, 0. et al., 'Toward cell therapy using placenta-derived cells: disease mechanisms, cell biology, preclinical studies, and regulatory aspects at the round table', Stem Cells and Development, 2010, vol. 19, No. 2, pp. 143-154.
PCT International Preliminary Report of Patentibility for PCT Patent Application PCT/US2013/064146, dated Sep. 25,2014.
PCT International Search Report and Written Opinion for PCT Patent Application No. PCT/US13/63736, dated Aug. 12, 2014.
PCT International Search Report and Written Opinion for PCT Patent Application No. PCT/US2014/012141, dated May 20, 2014.
Rennert et al. Stem Cell Recruitment After Injury; Lessons for Regenerative Medicine; Regen Med. Nov. 2012, 7(6): 833-850.
Russo A, et al., "The effects of different preservation processes on the total protein and growth factor content in a new biological product developed from human amniotic membrane." Cell and tissue banking 2012, 13:353-361.
Serena T, et al., "Clinical Research: Dehydrated human amniotic membrane dHAM) treatment of lower extremity venous ulceration (CR23)." In SAWC Annual Spring Meeting; Atlanta, GA. 2012.
Sheikh E.S., et al., "Use of dehydrated human amniotic membrane allografts to promote healing in patients with refractory non healing wounds" International Wound Journal (2014), 11:711-717.
Smiell J.M., et al., "Efficacy and safety of becaplermin (recombinant human platelet-derived growth factor-BB) in patients with nonhealing, lower extremity diabetic ulcers: a combined analysis of four randomized studies." Wound repair and regeneration : official publication of the Wound Healing Society [and] the European Tissue Repair Society 1999, 7:335-346.
Steed D.L., et al. Amnion-derived cellular cytokine solution: a physiological combination of cytokines for wound healing. Eplasty 2008, 8:e18.
Subrahmanyam M., "Amniotic membrane as a cover for microskin grafts." British journal of plastic surgery 1995, 48:477-478.
Toda A, et al., "The potential of amniotic membrane/amnion-derived cells for regeneration of various tissues." Journal of Pharmacological Sciences 2007, 105:215-228.
Tonnesen M.G., et al., "Angiogenesis in wound healing." The journal of investigative dermatology Symposium proceedings / the Society for Investigative Dermatology, Inc [and] European Society for Dermatological Research 2000, 5:40-46.
Uberti M.G., et al., "Amnion-derived cellular cytokine solution (ACCS) promotes migration of keratinocytes and fibroblasts." Annals of plastic surgery 2010, 64:632-635.
Ueta M., "Immunosuppressive properties of human amniotic membrane for mixed lymphocyte reaction." Clinical and experimental immunology 2002, 129:464-470.
Werner S. et al. "Regulation of wound healing by growth factors and cytokines." Physiological reviews 2003, 83:835-870.
Wieman, T.J., et al.,"Efficacy and safety of a topical gel formulation of recombinant human platelet-derived growth factor-BB (becaplermin) in patients with chronic neuropathic diabetic ulcers. A phase III randomized placebo-controlled double-blind study." Diabetes care 1998, 21:822-827.
Zelen C.M., et al. "A prospective randomised comparative parallel study of amniotic membrane wound graft in the management of diabetic foot ulcers." International wound journal 2013, 10:502-507.
O'Keefe, et al., Keratinocyte Growth-Promoting Activity From Human Placenta, Journal of Cellular Physiology. vol. 124, No. 3, Sep. 1985, pp. 439-445, 7 pages.

\* cited by examiner

ISOLATED PLACENTAL STEM CELL RECRUITING FACTORS

CROSS-REFERENCE TO RELATED APPLICATIONS

This application claims the benefit under 35 U.S.C. § 119(e) to U.S. provisional application Ser. No. 61/962,313 which was converted from U.S. nonprovisional application Ser. No. 13/745,642, filed Jan. 18, 2013; all of which are incorporated hereby by reference in their entirety.

BACKGROUND

Field of the Invention

This invention is directed, in part, to compositions comprising placental stem cell recruiting factors, more specifically, isolated placental stem cell recruiting factors and methods for isolating placental stem cell recruiting factors. In one embodiment, isolated placental stem cell recruiting factors are delivered to a site such as a diseased or injured organ and/or body part in an amount sufficient to recruit stem cells to the site.

State of the Art

Heretofore, modified placental tissue has been used to treat a diseased or injured internal organ or body part. However, such use has been limited by the amount of tissue available and the size of the organ or body part. As a general rule, the minimum amount of modified placental tissue to elicit the desired result has been used. For example, in one embodiment, the placental tissue is used as a barrier layer between organs so as to prevent adhesion formation. See, for example, U.S. Publ. No. 2010/0104539. In such cases, the modified placental tissue successfully provides an exogenous therapeutic effect.

It is well understood that a more successful therapeutic outcome is achieved when the treatment regimen includes not only the exogenous therapeutic effect but also an endogenous therapeutic effect. That is to say that patients who are able to cooperatively couple an exogenous therapeutic agent with their body's own ability to heal itself will achieve a better outcome. One mechanism for endogenous healing is the recruitment of stem cells to the injured or diseased organ site. However, such an in vivo recruitment has been exceptionally difficult to achieve. Accordingly, there is a need for compositions and methods for preparing compositions comprising placental stem cell recruiting factors that can be applied to a delivery site in a sufficient amount so as to recruit stem cells to the delivery site.

SUMMARY OF THE INVENTION

This invention is based, in part, on the discovery that application of a sufficient amount of placental stem cell recruiting factors proximate to a diseased or injured body part of a patient surprisingly elicits stem cell recruitment to the site of the diseased or injured body part. This invention is further based on the discovery that the delivery of stem cell recruiting factors isolated from modified placental tissue proximate to a diseased or injured body part of a patient in a sufficient amount achieves stem cell recruitment to the diseased or injured body part.

Accordingly, in one aspect of this invention there is provided a composition comprising isolated placental stem cell recruiting factors. These isolated recruiting factors can be employed to a diseased or injured body part to promote stem cell recruitment in vivo.

In another aspect of this invention, there is provided a composition comprising isolated placental stem cell recruiting factors provided in conjunction with modified placental tissue or an extract of a placental tissue to increase the concentration of stem cell recruiting factors present in the modified placental tissue or extract. In some aspects, the modified placental tissue is a placental tissue graft. In other aspects, the modified placental tissue is micronized. In another aspect, the modified placental tissue is an extract derived from placental tissue. In yet another aspect, the modified placental tissue comprises amnion, chorion, intermediate tissue layers or combinations thereof.

In a further aspect of this invention, the composition is provided in the form of a solution or a suspension. In one embodiment, there is provided an injectable composition comprising aqueous isolated placental stem cell recruiting factors in an amount sufficient to recruit stem cells in vivo. In another embodiment, the injectable composition contains a localizing agent which allows for localized retention of the solution or suspension at the site of delivery, thereby permitting the prolonged release of the stem cell recruiting factors. Exemplary localizing agents may include thixotropic agents, phase changing agents and the like.

In another aspect of this invention, there is provided a composition comprising lyophilized isolated placental stem cell recruiting factors in an amount sufficient for the in vivo recruitment of stem cells.

These and other aspects of this invention are further described herein.

BRIEF DESCRIPTION OF THE DRAWINGS

The accompanying drawings, which are incorporated in and constitute a part of this specification, illustrate several aspects described below.

DETAILED DESCRIPTION OF THE INVENTION

Figure 1:
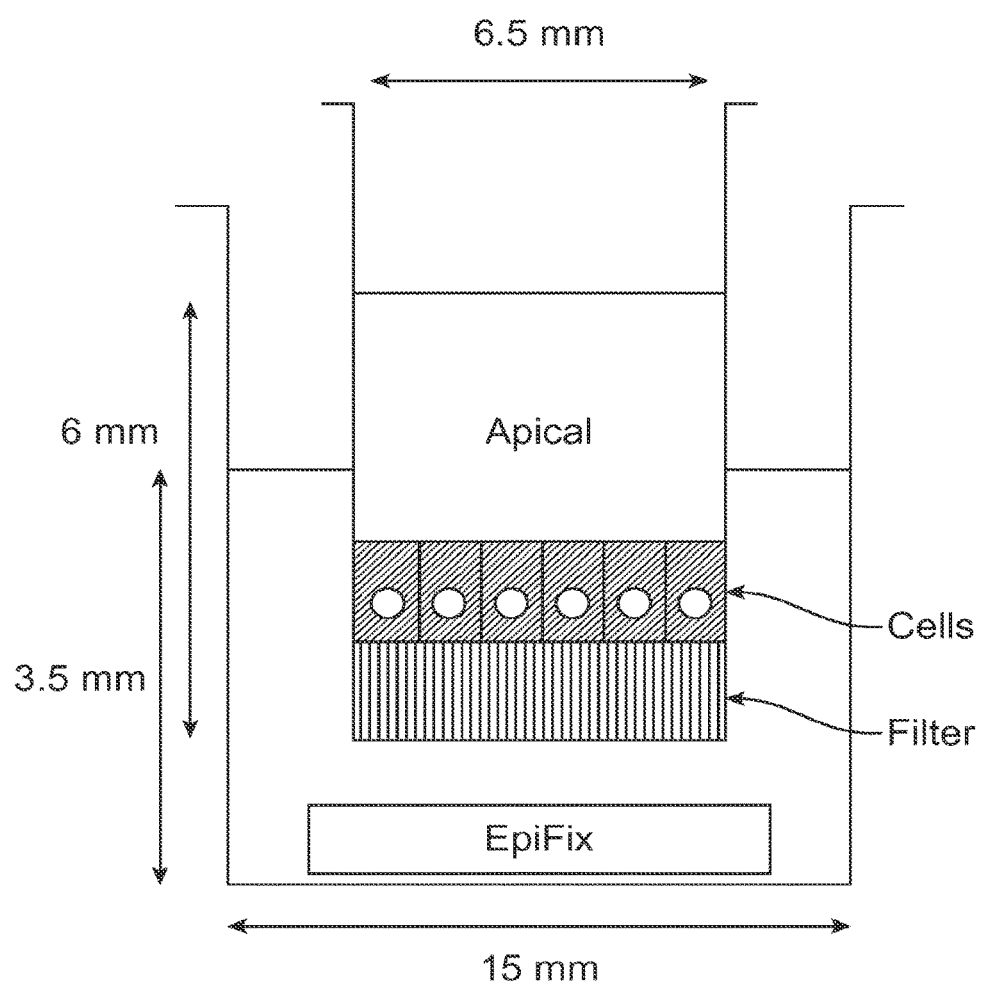
FIG. 1 shows a schematic for a cell culture insert for stem cell migration assays described in Example 1.

Before this invention is disclosed and described, it is to be understood that the aspects described below are not limited to specific compositions, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" or "patient" as used herein refers to any vertebrate organism including, but not limited to, mammalian subjects such as humans, farm animals, laboratory test animals, domesticated pets and the like.

The term "amnion" as used herein includes amniotic membrane where the intermediate tissue layer is intact or has been substantially removed.

The term "organ" as used herein is used to have an ordinary meaning in the art, and refers to organs constituting animal viscera in general.

The term "body part" as used herein refers to any portion of a body of a subject, including tissue(s) and organs, and also body parts which are not generally referred to as organs provided that such body parts are amenable to treatment with placental growth factors. Exemplary body parts include, but are not limited to, bone, cartilage, tendon, ligament, retina, peripheral nerve, peripheral nerve sheath, small intestine, large intestine, stomach, skeletal muscle, heart, liver, lung and kidney.

The term "diseased" as used herein refers to an organ and/or body part that is characterized as being in a disease state, or susceptible to being in a disease state, wherein the disease is amenable to treatment with placental growth factors.

The term "injured" as used herein is used to have an ordinary meaning in the art, and includes any and all types of damage to an organ and/or body part, wherein the injury is amenable to treatment with placental growth factors.

The term "modified placental tissue" refers to any and all components of placental tissue including whole placental tissue that has been modified by cleaning, disinfecting, and/or segmenting the tissue as well as to separated components of placental tissue such as amnion, chorion, the umbilical cord, and the like. Modified tissue may maintain cellular layers, such as the epithelial layer and/or the fibroblast layer. Modified placental tissue may include further modification, such as lamination of one or more layers of placental tissue, micronization of placental tissue, chemisorption or physisorption of small molecules, proteins (e.g. growth factors, antibodies), nucleic acids (e.g. aptamers), polymers, or other substances.

The term "extract of a placental tissue" refers to a composition, such as a solution or a lyophilized solid, comprising one or more of the biological factors present in a placental tissue or modified placental tissue and substantially free of the placental tissue or cell materials. Such extracts include those described in U.S. patent application Ser. No. 13/744,331, filed on Jan. 17, 2013, titled "NON-SURGICAL, LOCALIZED DELIVERY OF COMPOSITIONS FOR PLACENTAL GROWTH FACTORS," and U.S. Provisional Application No. 61/849,838, filed on Jan. 18, 2013, titled "METHODS FOR TREATING CARDIAC CONDITIONS," and can be prepared according to methods described therein. Both of these patent applications are hereby incorporated by reference in their entirety.

The term "placental growth factors" refers to that array of growth factors obtainable from modified placental tissue. The manner of obtaining such growth factors is not critical to the invention and include, by way of example only, aqueous extraction from the placenta, culturing of placental cells expressing such growth factors, and the like. The concentration of extracted growth factors can be increased by reducing the volume of water, saline, or buffer used to extract the growth factors, by addition of growth factors produced from placental cell cultures, and the like.

The term "stem cell" refers to a cell that can divide and differentiate into diverse specialized cell types and can self-renew to produce more stem cells. This term is intended to encompass both embryonic stem cells and adult stem cells.

The term "stem cell recruiting factors" refers to any and all factors that are capable of recruiting stem cells and causing them to migrate towards a source of such factors. Non-limiting examples of stem cell recruiting factors may be one or more CC chemokines, CXC chemokines, C chemokines, or $CX_3C$ chemokines.

The term "stem cell recruitment" refers to direct or indirect chemotaxis of stem cells to a modified placental tissue. The recruitment may be direct, wherein the placental stem cell recruiting factors (e.g. chemokines, which induce cell chemotaxis) in a modified placental tissue are released from the placental tissue and induce stem cells to migrate towards the placental tissue. In one aspect, the recruitment may be indirect, wherein stem cell recruiting factors in a modified placental tissue are released from the placental tissue which induce nearby cells to release factors (e.g. chemokines), that in turn induce stem cells to migrate towards the placental tissue. Still further, stem cell recruitment may embody both direct and indirect factors.

The terms "sufficient amount" or "effective amount" refers to an amount of placental growth factors that is sufficient to treat an injured or diseased organ or body part. The "sufficient amount" will vary depending on a variety of factors, such as but not limited to, the type and/or amount of the placental tissue or extract of a placental tissue used, the type and/or size of the intended organ and/or body part to be treated, the severity of the disease or injury to the organ and/or body part to be treated and the administration route. The determination of a "sufficient amount" can be made by one of ordinary skill in the art based on the disclosure provided herein.

The term "proximate to" as used herein means adjacent to, or contacting a body part such that the composition the composition exerts the desired effect. For example, modified placental tissue proximate to the heart means that the placental tissue may be on or in the heart, or within 1-2 cm of the heart, but still close enough to effect stem cell recruitment. In general, "proximate to" means that the modified placental tissue is placed sufficiently close so as to recruit stem cells to the diseased or injured organ and/or body part. Such a distance is generally within the skill of the art but preferably is within 3 cm, 2 cm, or 1 cm of the organ or body part, including on or in the body part.

The term "contact" or "contacting" means that the composition is on or in the body part.

The term "exogenous" refers to substances that are not naturally occurring to a body part being treated, including allograft tissue, such as modified placental tissue.

The term "endogenous" refers to autologous biological substances from a subject.

As used herein, the term "bioerodible," which is used herein interchangeably with the term "biodegradable," refers to a biocompatible material that gradually decomposes, dissolves, hydrolyzes and/or erodes in situ, or that is susceptible to degradation into smaller components or molecules in a living organism over a prolonged period of time, for example, over days or months, such that the material is harmless to the living organism under normal living conditions. Generally, the "bioerodible" polymers herein are polymers that are hydrolyzable, and bioerode in situ primarily through hydrolysis. Preferably, the smaller components or molecules are biocompatible to a patient.

As one of ordinary skill in the art would understand, the degradation of the material results in a continuous release of a therapeutic amount of placental growth factors incorporated in the material over a prolonged period of time, such as about 3 days, about 5 days, about 10 days, about 15 days, about 20 days, about 25 days, about 30 days, about 2 months, about 3 months, about 4 months, about 5 months, or about 6 months. A desired release rate can be determined and/or achieved by adjusting the initial concentration of the growth factors incorporated in the bioerodible or biodegradable mass and the degradation rate of the mass.

Titles or subtitles may be used in the specification for the convenience of a reader, which are not intended to influence the scope of the present invention. Additionally, some terms used in this specification are more specifically defined below.

Compositions and Methods

This invention is predicated in part on the discovery that application of a sufficient amount of a composition comprising placental stem cell recruiting factors in treating a diseased or injured body part provides not only an exogenous treatment regimen but surprisingly also promotes an endogenous response which results in stem cell recruitment to the body part to be treated. In this regard, it has been discovered that placental stem cell recruiting factors can be isolated from placental cells and used either alone, or in conjunction with modified placental tissue or extracts of placental tissue for increased stem cell recruitment, or combined with other conventional wound care devices such as collagen (including collagen sutures), hyaluronic acid and the like. In one embodiment, the stem cell recruited is a haematopoietic stem cell (HSC). In another embodiment, the stem cell recruited is a mesenchymal stem cell (MSC). In another embodiment, the stem cell recruited is bone marrow derived stem cell.

In one embodiment, the enhancement refers to a decrease in the time required to recruit stem cells or an increase in the number of stem cells recruited to a particular site in the body. In another embodiment, the enhancement refers to any and all benefits derived from a local concentration of stem cells, including but not limited to, an increase in therapeutic effects such as faster healing, reduced scarring, reduced side effects and the like. Additional therapeutic effects and other contemplated benefits are described herein.

Further aspects of the disclosure relate to compositions comprising isolated placental stem cell recruiting factors in an amount sufficient to recruit stem cells in vivo. Other aspects relate to compositions comprising isolated placental stem cell recruiting factors in combination with modified placental tissue or an extract of placental tissue in an amount sufficient to recruit stem cells in vivo. Further aspects relate to lyophilized or aqueous compositions comprising isolated placental stem cell recruiting factors in an amount sufficient to recruit stem cells in vivo. Another aspect relates to compositions comprising an extract comprised of isolated placental stem cell recruiting factors in an amount sufficient to recruit stem cells in vivo.

Placental stem cell recruiting factors may be directly isolated from the cells of the placenta. Such techniques are known in the art. Example 1 of the application describes a procedure suitable for culturing placental cells and isolating stem cell recruiting factors from the placental cells. The source of the placenta can vary as further described herein.

The recruiting factors may be isolated as described herein and/or by techniques known in the art. For example, in one embodiment, the placental derived stem cell recruiting factors are isolated from the media of cultures of placental cells. Isolation from the media of cultured placental cells provides for a therapeutic composition that is enriched in factors that recruit stem cells. When the factors are isolated from cultures of placental cells, the factors may be concentrated by techniques known in the art such as ultrafiltration, diafiltration, precipitation, chromatography, and the like. The placental stem cell recruiting factors may then be formulated into pharmaceutical compositions as described herein or lyophilized for increased stabilization during storage.

In one embodiment, the composition comprises placental stem cell recruiting factors isolated from modified placental tissue. In one embodiment, placental tissue may be modified as described in U.S. Ser. No. 61/683,698, including cleaning, separation of the amnion and chorion, removal or maintenance of the epithelial cell layer, decontamination, and dehydration. Dehydration may be accomplished using the drying apparatus or chemical dehydration, for example, as described in U.S. Ser. No. 13/691,509, filed Nov. 30, 2012. Both of which applications are incorporated herein by reference in their entirety. Each aspect of that process produces modified placental tissue for the purposes of this invention whether used alone or in combination. However, it is preferred that the modified placental tissue include at least the steps of cleaning and decontamination. As such, modified placental tissue preferably comprises placental tissue which has been cleaned and decontaminated and also includes placental tissue which has undergone one or more of separation of the amnion and chorion, removal of the epithelial cell layer, and dehydration.

In some embodiments of the present technology, the modified placental tissue is selected from amnion, chorion, or both amnion and chorion. In preferred embodiments, modified placental tissue does not include the umbilical cord.

Modified placental tissue may also be micronized into particles of a variety of sizes, for example, no more than about 300 microns in size, such as less than about 250 microns, less than about 200 microns, less than about 150 microns, less than about 100 microns, or less than about 50 microns. Micronized placental tissue may be sandwiched between one or more layers of a multilayer laminate, or on top of a laminate. Micronized placental tissue may also be added to single layer of modified placental tissue. See, for example, International Patent Application No. PCT/US2012/024798, filed Feb. 13, 2012, as well as U.S. Provisional Patent Application Ser. No. 61/683,700 filed Aug. 15, 2012 both of which are incorporated herein by reference in their entirety. It is also contemplated that micronized modified placental tissue can enhance the rate of stem cell recruitment in a particular body part. In some embodiments, micronized modified placental tissue is added to modified placental tissue, either a single layer of modified placental tissue, or in between a multi-layer laminate of placental tissue.

In some aspects, one or more stem cell recruiting factors that enhance stem cell chemotaxis and or recruitment may be added to modified placental tissue. In other aspects, stem cell recruiting factors can be added to micronized placental tissue.

Alternatively, stem cell recruiting factors may be added to layers of a laminate tissue graft. Thus, for example, cytokines, chemokines, growth factors, extracellular matrix components and other bioactive materials can be added to the modified placental tissue to enhance native stem cell recruitment. Specific non-limiting examples of stem cell recruiting factors may include one or more of the following: CC chemokines, CXC chemokines, C chemokines, or $CX_3C$ chemokines. Other stem cell recruiting factors may further include growth factors such as cc-Fibroblast Growth Factor (αFGF or αFGF-1), β-Fibroblast Growth Factor (βFGF-1 or βFGF-2), Platelet-Derived Growth Factor (PDGF), Vascular Endothelial Growth Factor (VEGF-A, B, C, D or E), Angiopoietin-1 and -2, Insulin-like Growth Factor (IGF-1), Bone Morphogenic Protein (BMP-2 and -7), Transforming Growth Factor-α and -β (TGF-α and TGF-β) Epidermal Growth Factor (EGF), Connective Tissue Growth Factor (CTGF), Hepatocyte Growth Factor (HGF), Human Growth Hormone (HGH), Keratinocyte Growth Factor (KGF), Tumor Necrosis Factor-α (TNF-α), Leukemia Inhibitory Factor (LIF), Nerve Growth Factor (NGF), Stromal cell derived factor 1 (SDF-1α), Granulocyte Macrophage Colony Stimulating Factor (GM-CSF) and other factors as is known in the art.

In some embodiments, the composition comprising placental stem cell recruiting factors is provided in an injectable form which may further include a pharmaceutically acceptable carrier. Suitable pharmaceutically acceptable carriers include, but are not limited to, such as water, a buffer (e.g., phosphate buffered saline (PBS), citrate buffer, etc.), water-soluble organic solvents (e.g., polyethylene glycol 300, polyethylene glycol 400, ethanol, propylene glycol, glycerin, N-methyl-2-pyrrolidone, dimethylacetamide, and dimethylsulfoxide), organic liquids/semi-solids (beeswax, d-tocopherol, oleic acid, medium-chain mono- and diglycerides), non-ionic surfactants (polyethoxylated castor oils (e.g., Cremophor EL, Cremophor RH 40, Cremophor RH 60), polysorbate 20, polysorbate 80, poloxamer 188, poloxamer 407, d-tocopherol polyethylene glycol 1000 succinate, polyethylene glycol (15)-hydroxystearate, sorbitan monooleate, oleoyl polyoxyl-6 glycerides, linoleoyl polyoxyl-6 glycerides, caprylocaproyl polyoxyl-8 glycerides, Gellucire® 44/14, Softigen® 767, and mono- and di-fatty acid esters of PEG 300, 400, or 1750, etc.), a lipid (e.g., castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil), cyclodextrin (such as α-cyclodextrin, β-cyclodextrin, and γ-cyclodextrin, hydroxypropyl-β-cyclodextrin, and sulfobutylether-β-cyclodextrin), and phospholipids (e.g., phosphatidylcholine, phosphatidylethanolamine, phosphatidylserine, distearoylphosphatidylglycerol, 1-dimyristoylphosphatidylcholine, 1-dimyristoylphosphatidylglycerol, etc.), or a mixture thereof.

In some embodiments, the composition forms a localized mass when applied to or proximate to said diseased and/or injured body part with a localization agent which allows for localized retention of the solution or suspension at the site of delivery, optionally for extended and/or continuous release of the biological factors in the composition. Such agents include thixotropic agents, phase changing agents, and the like. These compositions are in an injectable form at ambient conditions and form a viscous or gel-like bioerodible or biodegradable mass in vivo which limits transport away from the site of delivery and allows for the diffusion of the biological factors from the mass formed over a period of time.

In some embodiments, localization agents, such as thixotropic agents, phase changing agents, and the like, may include but not limited to, hydrogel, bioerodible, biocompatible polymer, and collagen gels. The presence of one or more localization agents in the compositions of this invention allows the compositions to have certain viscosity such that the compositions are locally retained for a period of time upon administration or injection. It is within the purview of one of ordinary skill in the art to determine the suitable viscosity of the compositions. In some aspects, the compositions have a viscosity between about 5 cP to about $1 \times 10^8$ cP, or about 5 cP to about $1 \times 10^6$ cP, or about 5 cP to about $1 \times 10^5$ cP, or about 5 cP to about $1 \times 10^4$ cP, or about 5 cP to about $1 \times 10^3$ cP, or about 6 cP to about 9500 cP at 25° C.

The hydrogels useful in the compositions of this invention can be chemically and/or physically cross-linked hydrogels. In situ chemical cross-linking is obtained, e.g., via photo-initiated, redox-initiated or Michael-type addition polymerization that preferably involve covalent bond formation. Physically cross-linked hydrogels self-assemble under external stimuli and do not rely on covalent bond formation. Temperature, pH, ion concentration, and hydrophobic interactions are certain of the external stimuli useful for such self-assembly and for the immobilization of such hydrogels.

Exemplary polymers suitable for the use in the composition of the present invention include polylactides, polyglycolides, poly(caprolactone), polyanhydrides, polyamines, polyesteramides, polyorthoesters, polydioxanones, polyacetals, polyketals, polycarbonates, polyphosphoesters, polyorthocarbonates, polyphosphazenes, succinates, poly(malic acid), poly(amino acids), polyvinylpyrrolidone, polyethylene glycol, polyhydroxycellulose, polyphosphoesters, polysaccharides, chitin, chitosan, hyaluronic acid, and copolymers, terpolymers and mixtures thereof.

Collagens can be used include, for example, alkaline treatment of insoluble collagen extracted from various animals, or by treating with enzyme such as pepsin, trypsin, chymotrypsin, papin or pronase. There are no particular restrictions on the origin of the collagen, and typically collagen can be used that is obtained from the skin, bone, cartilage, tendon or organs, etc. of birds or mammals, Since collagen allows the obtaining of a suitable consistency without heating, preparation can be made easily in the case of gelation. In addition, collagen has a high molecular weight, it more closely resembles living body tissue, has considerable physiological activity, and therefore promotes healing in the case of using on a wound, resulting in a further therapeutic effect in combination with the modified placental tissue. Collagen can be flexible after curing and requires only a short time for crosslinking, in other words, requires only a short time for gelation. Collagen solution can also be made by dissolving in a non-toxic solvent respect to the living body, examples of which include water, physiological saline, a buffer such as borate buffer, or an aqueous solution containing a salt such as sodium chloride, sodium bromide and potassium bromide, or protein, sugar or lipid, etc.

The collagen can also form a gel even in the presence of moisture such as that in blood or humor, and can demonstrate a high degree of adhesiveness with respect to living body tissue. Collagen solutions used in the present invention can be made at various concentrations, neutralized and prepared for injection. In various aspects, collagen at 0.2 mg/mL, 0.5 mg/mL, 0.75 mg/mL, 1 mg/mL, 2 mg/mL, 3 mg/mL, 4 mg/mL, 5 mg/mL, 6 mg/mL, 7 mg/mL, 8 mg/mL, 10 mg/mL, 20 mg/mL, 30 mg/mL, 40 mg/mL and 50 mg/mL in solution can be used for injection. Upon injection into an organ, chilled collagen gels can thermogel as they reach body temperature or about 37° C.

Compositions which can form a localized mass with prolonged retention, as well as their preparation including the agents forming the compositions, such as the phase-changing agents and thixotropic agents, are further described in U.S. patent application Ser. No. 13/744,331, filed on Jan. 17, 2013, titled "NON-SURGICAL, LOCALIZED DELIVERY OF COMPOSITIONS FOR PLACENTAL GROWTH FACTORS," which is hereby incorporated by reference in its entirety.

In some embodiments, the injectable composition is delivered to the body part to be treated with needle injection or with a catheter, and the delivery is optionally monitored by ways such as endoscope or fluoroscopy.

In some embodiments, compositions comprising placental stem cell recruiting factors can be suspended in saline, sterile water, or any suitable buffer known in the art to form a suspension. Extracts of the compositions can also be prepared using conventional methods known in the art.

In some embodiments, the composition disclosed may further comprise modified placental tissue comprising structural collagens and ECM proteins, regenerative molecules and/or growth factors. In some embodiments, the composition comprises a sufficient amount of placental growth factors. In some embodiments, the placental growth factors are extracted from modified placental tissue in sufficient quantities so as to provide for an aqueous composition comprising growth factors optionally without the need to form a suspension with modified placental tissue particles. In an alternative embodiment, the composition is free of stem cells or stem cell recruitment factors. Such compositions can also be formulated so as to form localized mass with prolonged retention in vivo.

Compositions comprising growth factors are further described in U.S. patent application Ser. No. 13/744,331, filed on Jan. 17, 2013, titled "NON-SURGICAL, LOCALIZED DELIVERY OF COMPOSITIONS FOR PLACENTAL GROWTH FACTORS," which is hereby incorporated by reference in its entirety.

In addition to the selection of the components used to make the composition comprising a modified placental tissue, the size of the micronized particles present in the grafts can also vary depending upon their application. In certain aspects, micronized particles having a larger particle size can be used in several applications. For example, the micronized particles (e.g., micronized amnion/chorion tissue graft) having a particle size from 150 μm to 350 μm can be effective in wound healing where it is desirable to reduce or prevent scar formation and enhance soft tissue healing.

In compositions comprising micronized particles as described herein, the size of the micronized particles present in the compositions can also vary depending upon their application. In certain aspects, micronized particles having a larger particle size can be used in several applications. For example, the micronized particles (e.g., micronized amnion/chorion tissue graft) having a particle size from 150 μm to 350 μm can be used.

In another aspect, the compositions described herein are implanted proximal or internal to a diseased and/or injured body part in an amount sufficient to attract stem cells and promote endogenous healing. In various aspects, in order to attract stem cells to a damaged body part, a sufficient amount of placental stem cell recruiting factors is required before the stem cells migrate to the target body part. In this aspect, stem cell recruitment to a particular delivery site operates in a concentration-dependent manner. See, for example, U.S. Provisional Application Ser. No. 61/713,352, which is incorporated herein by reference in its entirety. Stated another way, the presence of a sufficient amount of placental stem cell recruiting factors correlates to a sufficient concentration of stem cell recruiting factors such that stem cell recruitment is achieved. In this regard, the compositions described herein comprising stem cell recruiting factors can be used in concentrated formulations with or without modified placental tissue for the enhanced recruitment of stem cells. In this regard, the compositions may lead to a decrease in the time required to achieve a therapeutic effect and/or a decrease in the amount of material required to achieve a therapeutic effect. It is contemplated that higher amounts or concentrations of stem cell recruiting factors (such as by using an extract comprising stem cell recruiting factors or addition of stem cell recruiting factors to the modified placental tissue) will facilitate stem cell recruitment.

In addition, as shown below in Example 2, it is contemplated that the use of compositions comprising stem cell recruiting factors in conjunction with modified placental tissue would further enhance stem cell recruitment either in a reduced time frame to achieve stem cell recruitment and/or the number of stem cells recruited over a given period of time. In various embodiments, the enhancement of stem cell recruitment is at least 5%, 10%, 20%, 30%, 40%, 50%, 60%, 70%, 90%, 100% or more, when compared to the subject not receiving a composition as described herein.

It will be appreciated that the actual amounts of modified placental tissue or placental tissue extract administered in a specified case will vary according to the specific tissue to be treated, the particular compositions formulated, the mode of application, and the degree of disease or injury in particular subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physician's Desk Reference, Barnhart Publishing (1999)).

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1—Cell Migration in the Presence of EpiFix®

Human mesenchymal stem cells (human MSC) were evaluated in cell culture in the presence of samples of EpiFix® to determine whether the EpiFix® would induce migration of the human MSC. EpiFix® is a layer of amnion and chorion with the epithelial layer intact.

Materials and Methods

Standard migration assays were performed in 24-well cell culture inserts with 8-μm pore membrane filters at the bottom of the insert (see FIG. 1; BD Biosciences). 24 hours prior to the start of the experiment, human MSCs (one donor, passage 3) were cultured in serum free media, and 300 μL, of 5 μg/mL fibronectin in PBS was placed into each cell culture insert to enable adsorption of fibronectin to the cell culture insert surface overnight.

Figure 2:
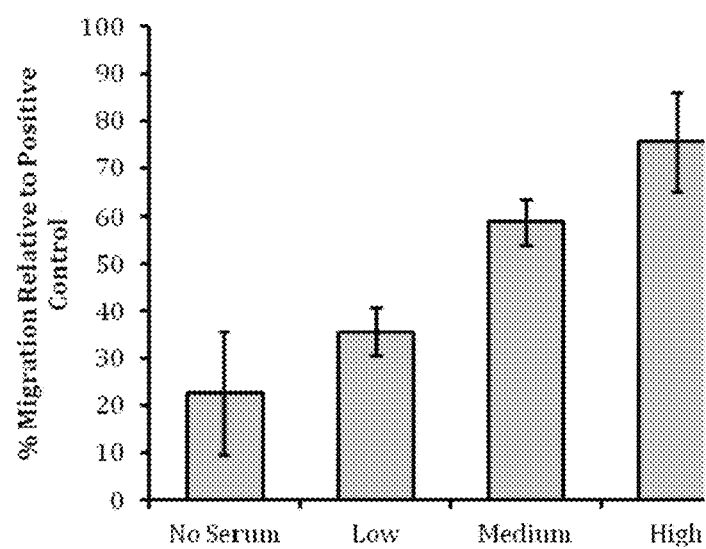
FIG. 2 shows a bar graph of percent cell migration in human mesenchymal stem cells (MSCs) cultured in the presence of various amounts of EpiFix®. Details are described in Example 1.

On the day of the experiment, 700 μL of serum-free culture medium was loaded into the bottom wells of the plate, followed by the addition of differently sized portions of sterilized EpiFix® (Low: 1.5-mm diameter disk; Medium: 4-mm diameter disk; High: 12×13 mm square, trimmed into 3-4 mm square pieces; n=6 EpiFix® tissue donors tested) (FIG. 2). One square centimeter of EpiFix® weighs 4 mg. Serum-free medium and medium with 10% fetal bovine serum (n=6) acted as negative and positive controls, respectively. Human MSCs (40,000 cells in 300 μL) were then loaded into the cell culture inserts and cultured for 24 hours. Then, both sides of the cell culture inserts were rinsed with PBS, and non-migrating cells in the upper portion insert were removed with a cotton-tipped applicator. Cells on the lower side of the insert plus the membrane filter were fixed in 10% formalin for 20 minutes, then rinsed and stained with hematoxylin for 5 min. The number of cells migrating through the membrane were counted on the lower surface of the membrane with an inverted microscope (Nikon TE2000; SPOT Software 4.6).

Data were normalized to the 10% FBS positive control and are expressed as mean±standard deviation of counted, migrated cells per 100× field micrograph for each sample well. Statistical comparisons were performed using a Box-Cox transformation to normalize data variance, followed by one-factor analysis of variance (ANOVA) with Tukey's honestly significant difference post-hoc test.

Results

The Low group (1.5 mm diameter disk) containing the smallest EpiFix® sample was not significantly different from the no serum negative control (see bar graph in FIG. 2). Both the Medium group (4 mm diameter disk) and the High group (12×13 mm square, trimmed into 3-4 mm square pieces) were statistically higher than the no serum control (about 60% and 75% migration relative to control; see FIG. 2), indicating that EpiFix® stimulated cell migration. The High group was not significantly different from the Medium group. The results indicate that the EpiFix® product contains one or more factors that attract human mesenchymal stem cells.

Example 2—Stem Cell Recruitment in Mice Receiving EpiFix® Implants

A study was undertaken to determine whether EpiFix® implanted in normal mice caused recruitment of stem/progenitor cells, focusing on mouse hematopoietic stem cells (HSCs) and mouse mesenchymal stem cells (mouse MSCs).

Materials and Methods

EpiFix® products from six donors were used for implantation in normal mice. A 5×5 mm square of EpiFix® was surgically placed subcutaneously in 4 month old FVB/NJ mice (weighing between about 23.50 g and about 30 g). Four mice were implanted per sample per time point. The time points were 3, 7, 14 and 28 days. The negative controls were normal skin and sham operated mice (surgical incision but no implant). Decellularized dermal matrix (acellular dermal matrix; ADM) was used as the comparative implant (Type I collagen, no cytokines). The implant and overlying skin was harvested for fluorescence-activated cell sorting (FACS).

Implants and overlying skin were harvested, cut into 1 mm$^2$ sections, and incubated in a 0.15% dispase/0.075% collagenase solution at 37° C. for 1 hour. After centrifugation, samples were stained with a lineage antibody cocktail as described below. CD31 antibody was added followed by Alexa Fluor 647 anti-rat secondary antibody. Phycoerythrin-Cy7-conjugated anti-CD45 antibody was incubated last. Samples were prepared and analyzed as described below.

Samples were incubated with a lineage negative (lin$^-$) antibody cocktail (Ter119/CD4/CD8a/Gr-1/CD45R/CD11b) followed by phycoerythrin-Cy5 anti-rat secondary antibody. For mesenchymal stem cell analysis, conjugated antibodies were added against CD45 (phycoerythrin-Cy7) and Sca-1 (fluorescein isothiocyanate). For hematopoietic stem cell analysis, conjugated antibodies were added against CD45 (phycoerythrin-Cy7), c-Kit (phycoerythrin), and Sca-1 (fluorescein isothiocyanate). Samples were incubated with antibodies for 30 minutes and then washed by adding 5 volumes of 2% fetal bovine serum in phosphate-buffered saline with 2 mM ethylenediaminetetraacetic acid. Cells were centrifuged and then re-suspended in propidium iodide for 1 minute at 4° C. Samples were analyzed using an LSR Flow Cytometer. Using CellQuest software), samples were gated for lin$^-$/Sca-1$^+$/CD45$^-$ to define mesenchymal stem cells and for lin$^-$/Sca-1$^+$/c-Kit$^+$/CD45$^+$ to define hematopoietic stem cells.

Results

Figure 3A:
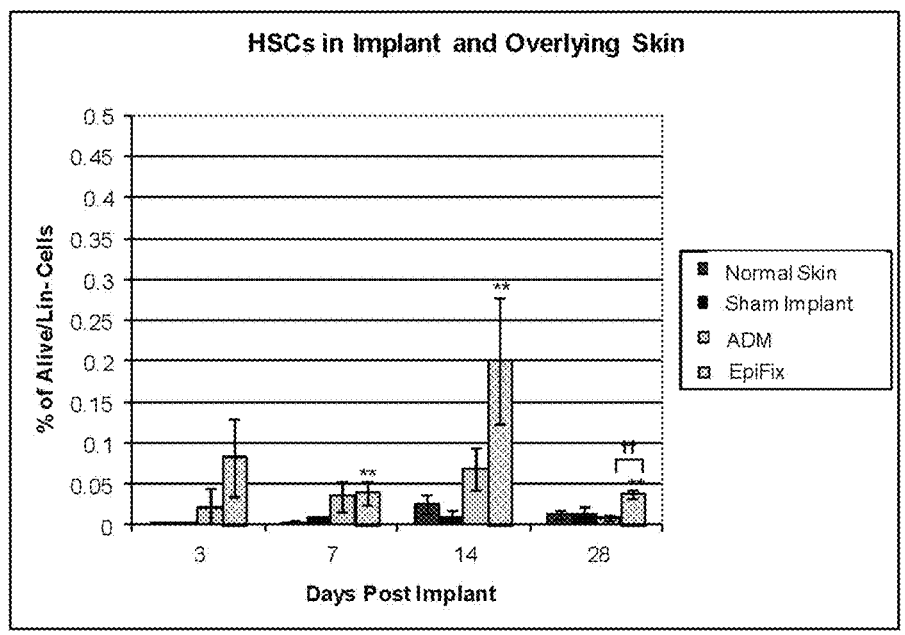
FIG. 3A shows a bar graph of percentage living/Lin⁻ mouse hematopoietic stem cells in normal skin, sham implant, acellular dermal matrix, and EpiFix® at 3, 7, 14, and 28 days post implant. Values shown are means+/−standard deviation, n=4 specimens.  indicates $p<0.05$ when comparing EpiFix® or control ADM to normal skin and sham implant via one-way ANOVA. †† indicates $p<0.05$ when comparing EpiFix® to control ADM via two tailed t-test.

Mouse HSCs were significantly increased following EpiFix® implantation compared to negative controls at days 7, 14 and 28 (see FIG. 3A). Mouse HSCs remained significantly increased in the EpiFix® samples at day 28 compared to ADM.

Figure 3B:
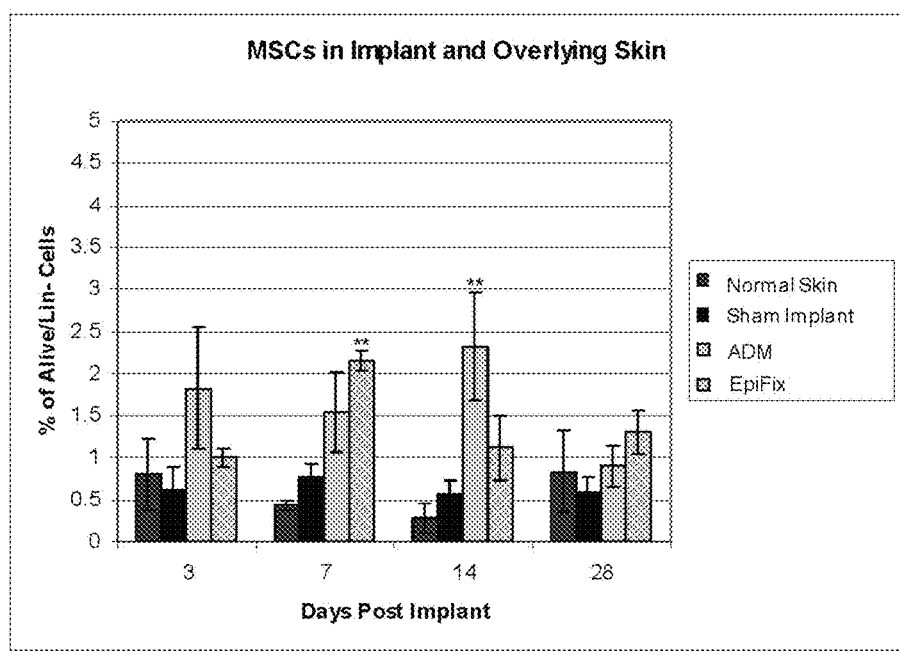
FIG. 3B shows a bar graph of percentage living/Lin⁻ mouse mesenchymal cells in normal skin, sham implant, acellular dermal matrix, and EpiFix® 3, 7, 14, and 28 days post implant. Values shown are means+/−standard deviations, n=4 specimens.  indicates $p<0.05$ when comparing EpiFix® or control ADM to normal skin and sham implant via one-way ANOVA. Details are described in Example 2.

Mouse MSCs were significantly increased following EpiFix® implantation compared to negative controls at day 7 (see FIG. 3B). The average percentages of mouse MSCs were increased at all time points compared to negative controls.

Thus the data described above show that EpiFix® implants effectively recruit both HSCs and MSCs in vivo in normal mice. The data also show that EpiFix® leads to longer term HSC recruitment than acellular dermal matrix (ADM), supporting the hypothesis of a cytokine mediated effect of EpiFix®.

Example 3—Stem Cell Characterization in Mice Receiving EpiFix® Implants

A study was undertaken to characterize stem cells recruited to EpiFix® implantation sites in mice, using flow cytometry and immunohistochemistry.

Materials and Methods

Sterile, Purion® processed EpiFix® in a 5×5 mm square patch was implanted subcutaneously through a skin incision on the backs of sixteen 4 month old FVB/NJ mice. Identical skin incisions were made in another sixteen mice to function as a control treatment (sham). For comparison with a collagen scaffold, a 5×5 mm square patch of decellularized human dermis (acellular dermal matrix; ADM) was implanted subcutaneously on the backs of sixteen mice. Un-operated mice were used as a source of "normal" back skin for the analyses.

The surgical site was removed at 3, 7, 14 and 28 days following implantation for analyses of stem cells. Four animals/group were used at each time point. Stem cells were identified with two distinct methods: Fluorescence-activated cell sorting (FACS) and immunohistochemistry (IHC). For the FACS analysis, all cells were isolated from the amnion and associated regenerated tissue. The cells were fluorescently labeled with antibodies to specific stem cell markers. The identity and number of each cell type were determined with a flow cytometer.

For the immunohistochemical analyses, the membrane and associated regenerated tissue was fixed, sectioned for slides, and stained with specific antibodies to stem cells. Two antibodies were used for the immunohistochemistry: anti-CD34, which specifically detects hematopoietic progenitor cells (HPC), and reacts with dermal progenitor cells, endothelial cells, dendritic cells; and anti-CD31, which detects endothelial cells. The stained tissue sections were examined microscopically and the presence and number of specific stem cell types were measured. For the experimental analysis, the relative number of each cell type was counted. The results were calculated as the percentage of each cell type (no. of immunostained cells/total number of cells). Two areas were analyzed immunohistochemically for cell recruitment: the tissue surrounding the implant and the implant itself.

Results

Hematopoietic progenitor cell (HPC) levels were significantly elevated in tissue surrounding EpiFix® implants at days 14 and 28 compared to negative controls. Hematopoietic progenitor cells were significantly increased in the tissue surrounding the EpiFix® implant at days 14 and 28 compared to collagen scaffold ADM control.

Progenitor cells were recruited into the EpiFix® implant. Intra-implant hematopoietic progenitor cells peaked at day 14 in the EpiFix® implant, and remained elevated at day 28. Average intra-implant hematopoietic progenitor cells were increased in the EpiFix® implant at days 14 and 28 compared to control ADM. Progenitor cells were not recruited into the ADM control implant.

Vascularization of the EpiFix® implant steadily increased from day 14 to day 28. The amount of new vessel formation in the EpiFix® implant was significantly greater than that in the ADM control on day 28.

These data establish that EpiFix® contains one or more factors that recruit both hematopoietic stem cells and mesenchymal stem cells to the site of injury. More of these stem cells were found in the EpiFix® membrane and associated regenerated tissue than in the sham. EpiFix® was significantly more effective than the control decellularized collagen scaffold in recruiting progenitor cells to colonize the implant site. There were more progenitor cells in the EpiFix® membrane than in the control collagen scaffold.

EpiFix® also induced new blood vessel formation in the associated regenerated tissue and the EpiFix® membrane itself. Vascularization in the EpiFix® membrane was significantly higher than in the collagen scaffold control.

Example 4—Isolation of Stem Cell Recruiting Factors from Placental Tissues

To isolate stem cell recruiting factors from placental cells in culture, the following protocol can be used.

Amnion membranes are cut into small pieces and digested twice in 0.05% trypsin:EDTA (Gibco) for 40 min at 37° C. Following inactivation of trypsin with newborn calf serum, dispersed cells are washed in DMEM/F12 medium (available commercially from Gibco) and erythrocytes are lysed in hypotonic solution. Cells that are positive for epithelial markers such as cytokeratin-7 and 8/18 (available commercially from Dako, Denmark) by flow cytometry and display a cobblestone epithelial morphology in culture are used for in vivo and in vitro studies.

Cells are grown on cell culture plates to about 70% or 80% confluence and fresh media is added. Placental stem cell recruiting factors are isolated by collecting the media in a sterile conical tube each day for a 5 day period. The media is then filtered to remove any cells or cell debris. The placental stem cell recruiting factors in the isolated media are concentrated by ultrafiltration using a 100 kDa MWCO.

The compositions comprising the placental stem cell recruiting factors can be formulated into microspheres as previously described.

Example 5—Stem Cell Recruitment in Mice Receiving Isolated Placental Stem Cell Recruiting Factors To determine whether compositions comprising isolated placental stem cell recruiting factors implanted in normal mice cause recruitment of stem/progenitor cells, the following protocol was used.

Four mice were implanted with a composition containing isolated placental stem cell recruiting factors in a concentrated composition and evaluated on a per sample basis per time point. The time points are 1, 2, 4, 6, 8, 10, 15, 20, and 28 days. The negative controls are normal skin and sham operated mice (surgical incision but no implant). Decellularized dermal matrix (acellular dermal matrix; ADM) and/or micronized placental tissues without isolated placental stem cell recruiting factors can be used as the comparative implant (Type I collagen, no cytokines). The implant and overlying skin is harvested for fluorescence-activated cell sorting (FACS).

Implants and overlying skin are harvested, cut into 1 $mm^2$ sections, and can be incubated in a 0.15% dispase/0.075% collagenase solution at 37° C. for 1 hour. After centrifugation, samples are stained with a lineage antibody cocktail as described below. CD31 antibody is added followed by Alexa Fluor 647 anti-rat secondary antibody. Phycoerythrin-Cy7-conjugated anti-CD45 antibody was incubated last. Samples are prepared and analyzed as described below.

Samples are incubated with a lineage negative ($lin^-$) antibody cocktail (Ter119/CD4/CD8a/Gr-1/CD45R/CD11b) followed by phycoerythrin-Cy5 anti-rat secondary antibody. For mesenchymal stem cell analysis, conjugated antibodies are added against CD45 (phycoerythrin-Cy7) and Sca-1 (fluorescein isothiocyanate). For hematopoietic stem cell analysis, conjugated antibodies are added against CD45 (phycoerythrin-Cy7), c-Kit (phycoerythrin), and Sca-1 (fluorescein isothiocyanate). Samples are incubated with antibodies for 30 minutes and then washed by adding 5 volumes of 2% fetal bovine serum in phosphate-buffered saline with 2 mM ethylenediaminetetraacetic acid. Cells are centrifuged and then re-suspended in propidium iodide for 1 minute at 4° C. Samples can be analyzed using an LSR Flow Cytometer. Using CellQuest software), samples are gated for lin$^-$/Sca-1$^+$/CD45$^-$ to define mesenchymal stem cells and for lin$^-$/Sca-1$^+$/c-Kit$^+$/CD45$^+$ to define hematopoietic stem cells.

It is believed that compositions comprising isolated placental stem cell recruiting factors in a concentrated composition will be more effective in recruiting HSCs and MSCs. For example, the increase in concentration of stem cell recruiting factors may decrease the time required for stem cell recruitment to the site of injection. It is contemplated that stem cell recruitment is seen 1, 2, 3, 4, 5, 6, 7, 8, 9, or 10 days after injection of the composition.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A composition comprising
    a localization agent,
    isolated placental stem cell recruiting factors in an amount sufficient to recruit stem cells to a diseased or injured organ or body part in vivo, and
    a modified placental tissue, said modified placental tissue comprising a laminated tissue graft comprising at least two layers selected from the group consisting of amnion, chorion, and a combination thereof, said layers directly laminated to each other, wherein the modified placental tissue comprises a fibroblast cellular layer;
    wherein said localization agent is selected from the group consisting of a hydrogel, a biocompatible polymer, a thixotropic agent, a phase-changing agent, and a collagen gel.

2. The composition of claim 1, wherein said modified placental tissue is a modified tissue graft.

3. The composition of claim 1, wherein said modified placental tissue is micronized.

4. The composition of claim 1, wherein said composition is provided in an aqueous solution.

5. The composition of claim 1, wherein said composition is provided in an injectable formulation.

6. The composition of claim 1, wherein said localization agent is a thixotropic agent or a phase changing agent.

7. The composition of claim 6, wherein said thixotropic agent is selected from the group consisting of hyaluronic acid, collagen gel, thrombin gel, fibrin gel and fibrin glue.

8. The composition of claim 6, wherein said phase changing agent is a gel forming agent.

9. The composition of claim 8, wherein said gel forming agent is a copolymer or tripolymer of oxyethylene and oxypropylene units.

10. The composition of claim 3, wherein said composition is provided in an injectable formulation.

* * * * *